(12) United States Patent
Bonheyo et al.

(10) Patent No.: US 10,360,667 B2
(45) Date of Patent: Jul. 23, 2019

(54) BIOLOGICAL MATERIAL FOULING ASSESSMENT SYSTEMS AND METHODS

(71) Applicant: Battelle Memorial Institute, Richland, WA (US)

(72) Inventors: George T. Bonheyo, Sequim, WA (US); Curtis J. Larimer, Richland, WA (US); Eric M. Winder, Sequim, WA (US); Raymond S. Addleman, Benton City, WA (US); Robert T. Jeters, Sequim, WA (US); Matthew S. Prowant, Richland, WA (US); Anthony D. Cinson, Hickory, NC (US)

(73) Assignee: Battelle Memorial Institute, Richland, WA (US)

( * ) Notice: Subject to any disclaimer, the term of this patent is extended or adjusted under 35 U.S.C. 154(b) by 55 days.

(21) Appl. No.: 15/240,761

(22) Filed: Aug. 18, 2016

(65) Prior Publication Data
US 2017/0053391 A1   Feb. 23, 2017

Related U.S. Application Data

(60) Provisional application No. 62/207,017, filed on Aug. 19, 2015.

(51) Int. Cl.
*G06K 9/00* (2006.01)
*G06T 7/00* (2017.01)
(Continued)

(52) U.S. Cl.
CPC ......... *G06T 7/0002* (2013.01); *G01N 17/008* (2013.01); *G01N 33/52* (2013.01);
(Continued)

(58) Field of Classification Search
CPC .... G01N 33/52; G06K 9/0014; G06T 1/0007; G06T 7/00; G06T 7/408; G06T 7/0002; G06T 2207/30188
See application file for complete search history.

(56) References Cited

U.S. PATENT DOCUMENTS

| 6,606,394 B1 * | 8/2003 | Park ..................... G01N 21/88 382/108 |
| 8,629,210 B2 * | 1/2014 | Webster .................. C08F 2/38 524/505 |

(Continued)

FOREIGN PATENT DOCUMENTS

| EP | 2552099 | 1/2013 |
| WO | WO 2012/019133 | 2/2012 |

(Continued)

OTHER PUBLICATIONS

Martinez, Thomas, et al. "Algal growth inhibition on cement mortar: Efficiency of water repellent and photocatalytic treatments under UV/VIS illumination." International Biodeterioration & Biodegradation 89 (2014): 115-125.*

(Continued)

*Primary Examiner* — Shefali D Goradia
(74) *Attorney, Agent, or Firm* — Wells St. John P.S.

(57) ABSTRACT

Biological material fouling assessment systems and methods are described. According to one aspect, a biological material fouling assessment system includes processing circuitry configured to access image data of an image of a surface of a substrate which has been fouled with biological material, wherein the image data comprises intensity information regarding a plurality of pixels of the image, and wherein the processing circuitry is further configured to process the intensity information regarding the pixels of the image to generate information which is indicative of an amount of the (Continued)

fouling of the biological material upon the surface of the substrate.

31 Claims, 8 Drawing Sheets

(51) Int. Cl.
    *G06T 1/00*           (2006.01)
    *G01N 33/52*         (2006.01)
    *G01N 17/00*         (2006.01)
    *G06T 5/00*           (2006.01)
    *G06T 5/40*           (2006.01)

(52) U.S. Cl.
    CPC .......... *G06K 9/0014* (2013.01); *G06T 1/0007* (2013.01); *G06T 5/009* (2013.01); *G06T 5/40* (2013.01); *G06T 7/0004* (2013.01); *G06T 2207/10024* (2013.01); *G06T 2207/30188* (2013.01)

(56) References Cited

U.S. PATENT DOCUMENTS

| | | | |
|---|---|---|---|
| 9,342,876 B2* | 5/2016 | Glazoff | G06T 7/00 |
| 2004/0230117 A1* | 11/2004 | Tosaya | A61B 17/22004 600/439 |
| 2005/0037406 A1* | 2/2005 | De La Torre-Bueno | G01N 21/6428 435/6.12 |
| 2010/0330025 A1* | 12/2010 | Messersmith | A61L 27/34 424/78.17 |
| 2011/0305881 A1* | 12/2011 | Schultz | A61L 33/0088 428/195.1 |
| 2012/0112098 A1 | 5/2012 | Hoyt | |
| 2013/0027589 A1 | 1/2013 | Johansson | |
| 2014/0000346 A1* | 1/2014 | Hoek | B01D 61/025 73/38 |
| 2016/0253466 A1 | 9/2016 | Agaian et al. | |

FOREIGN PATENT DOCUMENTS

| | | |
|---|---|---|
| WO | WO 2015/054666 | 5/2015 |
| WO | WO PCT/US2018/047629 | 2/2018 |

OTHER PUBLICATIONS

WO PCT/US2016/047629 Search Rept., dated Nov. 25, 2016, Battelle Memorial Institute.
WO PCT/US2016/047629 Writ. Opin., dated Nov. 25, 2016, Battelle Memorial Institute.
Amaral et al., "Stalked Priotozoa Identification by Image Analysis and Multivariable Statistical Techniques", Analytical and Bioanalytical Chemistry 391, 2008, Germany, pp. 1321-1325.
Arora et al., "Multilevel Thresholding gor Image Segmentation Through a Fast Statistical Recursive Algorithm", Pattern Recognition Letters 29(2), 2008, Netherlands, 9 pages.
Baveye, "Comment on 'Evaluation of Biofilm Image Thresholding Methods'", Water Research 36, 2002, United Kingdom, pp. 805-806.
Bloem et al., "Fully Automatic Determination of Soil Bacterium Numbers, Cell Volumes, and Frequencies of Dividing Cells by Confocal Laser Scanning Microscopy and Image Analysis", Applied and Environmental Microbiology vol. 61, No. 3, 1995, United States, pp. 926-936.
Boulos et al. "LIVE/DEAD® BacLightTM: Application of a New Rapid Staining Method for Direct Enumeration of Viable and Total Bacteria in Drinking Water", Journal of Microbiological Methods 37, 1999, Netherlands, pp. 77-86.
Carpenter et al., "Cell Profiler: Image Analysis Software for Identifying and Quantifying Cell Phenotypes", Genome Biology vol. 7, Issue 10, Article R100, 2006, United Kingdom, 11 pages.
Costerton et al., "Bacterial Biofilms: A Common Cause of Persistent Infections", Science vol. 284, 1999, United States, pp. 1318-1322.
Costerton et al., "Introducing Biofilms", Biofilms 1, 2004, United Kingdom, pp. 1-4.
Costerton et al., "Microbial Biofilms", Annual Review of Microbiology 49, 1995, United States, pp. 711-745.
Cruz-Orive, "Unbiased Stereology: Three-Dimensional Measurement in Microscopy", Journal of Anatomy 194, 1999, United Kingdom, pp. 153-157.
Falkinham, "Surrounded by Mycobacteria: Nontuberculosis Mycobacteria in the Human Environment", Journal of Applied Microbiology 107, 2009, United Kingdom, pp. 356-367.
Flemming et al., "Marine and Industrial Biofouling", Springer Series on Biofilms vol. 4, Germany, 2009, 330 pages.
Heydorn et al., "Quantification of Biofilm Sturctures by the Novel Computer Program COMSTAT", Microbiology 146, 2000, United Kingdom, pp. 2395-2407.
Huang et al., "Optimal Multi-Level Thresholding Using a Two-Stage Otsu Optimization Approach", Pattern Recognition Letters 30, 2009, Netherlands, pp. 275-284.
Janknecht et al., "Online Biofilm Monitoring", Reviews in Environmental Science and Biotechnology 2, 2003, Netherlands, pp. 269-283.
Javed et al., "Techniques for Studying Initial Bacterial Attachment and Subsequent Corrosion of Metals", Corrosion & Prevention, 2013, Australia, 10 pages.
Kohler et al., "Multivariate Image Analysis of a Set of FTIR Microspectroscopy Images of Aged Bovine Muscle Tissue Combining Image and Design Information", Analytical and Bioanalytical Chemistry 389, 2007, Germany, pp. 1143-1153.
Kunjundzic et al., "Monitoring Protein Fouling on Polymeric Membranes using Ultra-Sonic Frequency-Domain Reflectometry", Membranes 1, 2011, Switzerland, pp. 195-216.
Liao et al., "A fast Algorith for Multi-Level Thresholding", Journal of Information Science and Engineering 17, 2001, Taiwan, pp. 713-727.
Otsu, "A Threshold Selection Method From Gray-Level Histograms", IEEE Transactions on Systems, Man and Cynbernetics vol. SMC-9, No. 1, 1979, United States, pp. 62-66.
Podlipec et al., "Cell-Scaffold Adhesion Dynamics Measued in First Seconds Predicts Cell Growth on Days Scale—Optical Tweezers Study", ACS Applied Materials and Interfaces 7, 2015, United States, pp. 6782-6791.
Raja et al., "Otsu Based Optimal Multilevel Image Thresholding Using Firefly Algorithm", Modelling and Simulation in Engineering, 2014, United States, 17 pages.
Selinummi et al., "Software for Quantification of Labeled Bacteria from Digital Microscope Images by Automated Image Analysis", BioTechniques vol. 39, No. 6, 2005, United States, pp. 859-862.
Sezgin et al., "Survey Over Image Thresholding Techhiques and Quantitative Performace Evalution", Journal of Electronic Imaging 13(1), 2004, United States, pp. 146-168.
Sieracki et al., "Evalution of Automated Threshold Selection Methods for Accurately Sizing Microscopic Fluorescent Cells by Image Analysis", Applied and Environmental Microbiology vol. 55, No. 11, 1989, United States, pp. 2762-2772.
Stanimirova et al., "Discrimination of Biofilm Samples Using Pattern Recognition Techniques", Analytical and Bioanalytical Chemistry 390, 2008 Germany, pp. 1273-1282.
Steiner et al., "Fluorescent Protein Conjugates", Chemical Reviews 62, 41961, United States, pp. 457-483.
Suzuki et al., "DNA Staining for Fluorescence and Laser Confocal Microscopy", Journal of Histochemistry & Cytochemistry 45(1), 1997, United States, pp. 49-53.
Taff et al., "Comparative Analysis of Candida Biofilm Quantitation Assays", Medical Mycology 50, 2012, United Kingdom, pp. 214-216.
Vincent, "Morphological Grayscale Reconstruction in Image Analysis: Applications and Efiicient Algorithms", IEEE Transactions on Image Processing vol. 2, No. 2, 193, United States, pp. 176-201.

(56) References Cited

OTHER PUBLICATIONS

Walker et al., "Biodegradation and Biosorption of Acid Anthraquinone Dye", Environmental Pollution 108, 2000, United Kingdom, pp. 219-223.
Wei et al., "An Intuitive Discussion on the Ideal Ramp Filter in Computed Tomography (I)", Computers and Mathematics with Applications 49, 2005, United Kingdom, pp. 731-740.
Wolf et al., "Optical and Spectroscopic Methods for Biofilm Examination and Monitoring", Reviews in Environmental Science and Biotechnology 1, 2002, Netherlands, pp. 227-251.
Yang et al., "Evaluation of Biofilm Image Thresholding Methods", Water Research vol. 35, No. 5, 2001, United Kingdom, pp. 1149-1158.
Zhang et al., "Density, Porosity, and Pore Structure of Biofilms", Water Research vol. 28, No. 11, 1994, United Kingdom, pp. 2267-2277.
ASTM International, "Standard Practice for Evaluating Biofouling Resistance and Physical Performance of Marine Coating Systems", ASTM Designation D6990-05, 2011, United States, 13 pages.
ASTM International, "Standard Practice for Testing Biofouling Resistance of Marine Coatings Partially Immensed", ASTM Designation D5479-94, 2013, United States, 2 pages.
ASTM International, "Standard Test Method for Evaluating Disinfectant Efficacy Against Pseudomonas Aeruginosa Biofilm Grown in CDC Biofilm Reactor Using Single Tube Method", ASTM Designation E2871-13, 2013, United States, 6 pages.
ASTM International, "Standard Test Method for Quantification of Pseudomonas Aeruginosa Biofilm Grown Using Drip Flow Biofilm Reactor with Low Shear and Continuous Flow", ASTM Designation E2647-13, 2013, United States, 6 pages.
ASTM International, "Standard Test Method for Quantification of Pseudomonas Aeruginosa Biofilm Grown with High Shear and Continuous Flow Using CDC Biofilm Reactor", ASTM Designation E2562-17, 2012, United States, 6 pages.
ASTM International, "Standard Test Method for Quantification of Pseudomonas Aeruginosa Biofilm Grown with Medium Shear and Continuous Flow Using Rotating Disk Reactor", ASTM Designation E2196-17, 2012, United States, 6 pages.
ASTM International, "Standard Test Method for Subjecting Marine Antifouling Coating to Biofouling and Fluid Shear Forces in Natural Seawater", ASTM Designation D4939-89, 2013, United States, 5 pages.
ASTM International, "Standard Test Method for Testing Antifouling Panels in Shallow Submergence", ASTM Designation D3623-78a, 2012, United States, 8 pages.
ASTM International, "Standard Test Method for Testing Disinfectant Efficacy Against Pseudomonas Aeruginosa Biofilm using the MBEC Assay", ASTM Designation D2799-17, 2012, United States, 9 pages.
Bancroft et al., "Theory and Practice of Histological Techniques", 7th Edition, Chapters 9-15, Churchill Livingstone, 2013, United States, 163 pages.
Dobretsov, "Marine Biofilms", In Biofouling, Chapter 9, Eds. Durr et al., Blackwell Publishing Ltd., 2010, Singapore, pp. 123-136.
Durr et al., "Biofouling and Antifouling in Aquaulture", In Biofouling, Chapter 19, Eds. Durr et al., Blackwell Publishing Ltd., 2010, Singapore, pp. 267-287.
Edyvean, "Consequences of Fouling on Shipping", In Biofouling, Chapter 15, Eds. Durr et al., Blackwell Publishing Ltd., 2010, Singapore, pp. 217-225.
Larimer et al., "A Method for Rapid Quantitative Assessment of Biofilms with Biomolecular Staining and Image Analysis", Analytical & Bioanalytical Chemistry vol. 408, No. 3, Jan. 2016, Germany, 11 pages.
Lewandowski et al., "Fundamentals of Biofilm Research", 2nd Edition, CRC Press, 2007, Boca Raton, pp. 14-18.
Sabnis, "Handbook of Biological Dyes and Stains: Synthesis and Industrial Applications", Wiley, 2010, United States, 537 pages.
Wistreich, "The Differentiation of Bacterial Groups by Staining Reactions", Section IV of Microbiology Laboratory: Fundamentals and Applications, Prentice Hall, 2003, United States, pp. 139-156.

\* cited by examiner

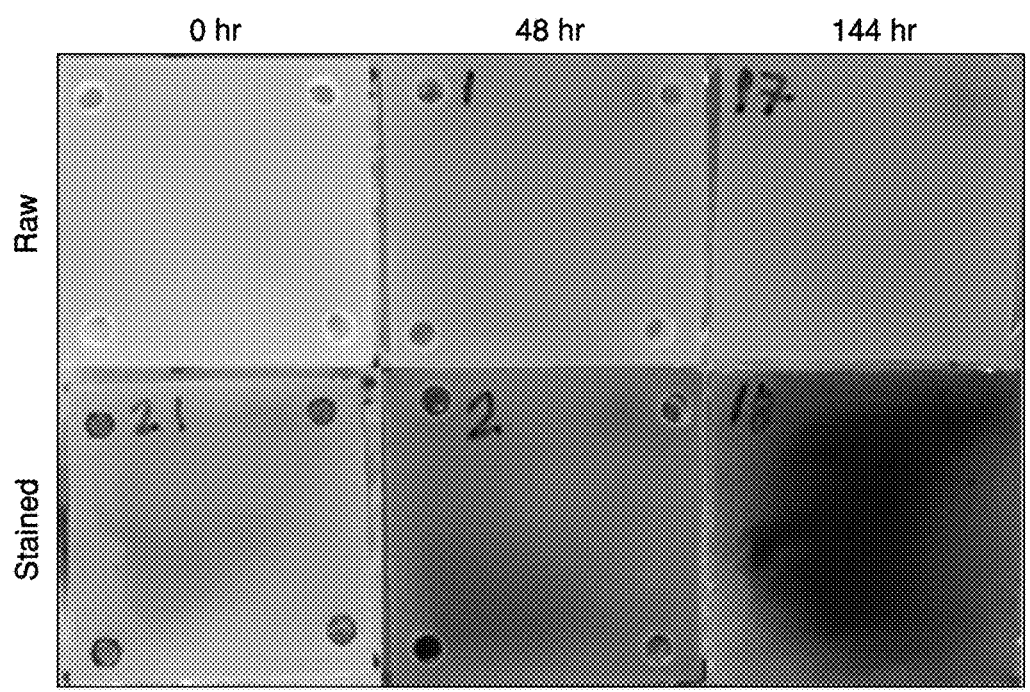
FIG. 3
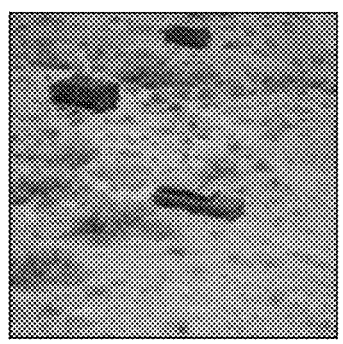 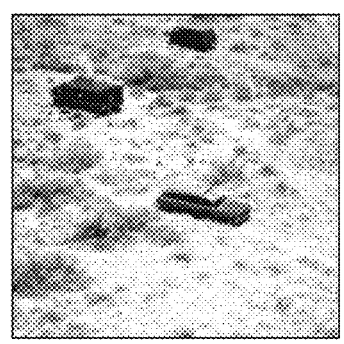 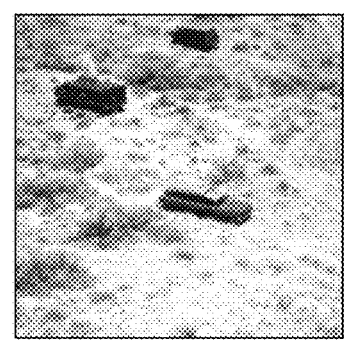
FIG. 4A     FIG. 4B     FIG. 4C

BIOLOGICAL MATERIAL FOULING ASSESSMENT SYSTEMS AND METHODS

RELATED PATENT DATA

This application claims the benefit of U.S. Provisional Patent Application Ser. No. 62/207,017, filed Aug. 19, 2015, titled "Digital Image Analysis System and Process for Assessment of Bacterial Fouling of Surfaces", the disclosure of which is incorporated herein by reference.

STATEMENT AS TO RIGHTS TO INVENTIONS MADE UNDER FEDERALLY-SPONSORED RESEARCH AND DEVELOPMENT

This invention was made with Government support under Contract DE-AC0576RL01830 awarded by the U.S. Department of Energy. The Government has certain rights in the invention.

REFERENCE TO A COMPUTER PROGRAM LISTING APPENDIX

This patent incorporates by reference the material in an ACHII text file having the name Computer Program Listing Appendix.txt, created Apr. 25, 2019 and having a size of 13.1 KB (13,485 bytes).

TECHNICAL FIELD

This disclosure relates to biological material fouling assessment systems and methods.

BACKGROUND OF THE DISCLOSURE

In natural aqueous environments, man-made interfaces are subjected to accumulation of unwanted biological fouling or biofouling. It is difficult to accurately quantify early-stage development of biofouling, particularly in situ, because they are typically composed of diverse groups of microscopic organisms and other organic material that form heterogeneous, soft, and often transparent structures.

Biofouling forms when organic matter (e.g., proteins, sugars, nucleic acids, lipids) and microorganisms settle on a surface and discharge a sticky matrix of polymeric substances that protect them and eventually attract or trap more or larger, multicellular fouling organisms (e.g., barnacles, mussels, algae). Biofouling may be harmful even in the earliest stages: thin layers of biofouling on medical implants routinely lead to full-fledged infections, and an increase in roughness of a ship's hull by as little as 10 µm can increase drag and affect fuel efficiency. Furthermore, fouling inhibits flow through industrial filters, exacerbates corrosion, reduces heat transfer efficiency, persists in water distribution networks, and otherwise permeates the built environment with deleterious effects. Often, fouling occurs in places that are not suited to traditional sanitary laboratory testing so quantifying biofouling growth in the environment is a challenge.

There are several American Society for Testing and Materials (ASTM) standards for the assessment of biofouling on marine antifouling coatings. However, these standards have limited applicability, require long-term data collection (up to 2 years), and are only semi-quantitative because they rely on subjective estimates of areal coverage based on visual inspection and on counting organisms of various fouling species (e.g., barnacles, oysters/mussels, tubeworms, algae, etc.). Since the methods are based on visual inspection, it is typically not possible to quantitatively evaluate the development of early-stage fouling. Subtle differences in this soft, transparent or semi-transparent, heterogeneous film of microorganisms cannot be distinguished with the naked eye, yet may serve as an important predictor of the development of fouling in the long term. Additionally, counting species does not correlate with the mass or volume of organic material present as the size of each individual organism can vary greatly depending in part upon the stage of development or age of the organism. Moreover, the conditioning film, biofilm, or slime layer often covers the full area of a sample surface but it typically does not do so evenly, so areal coverage can be a misleading measurement that may not accurately represent the progress of fouling development.

By contrast, there is a strong collection of ASTM standards for the evaluation of biofouling formation in laboratory settings with well-controlled exposure to a limited selection of microorganisms. These test methods serve as a model for improved quantification of marine biofouling; however, they are for laboratory evaluation and use specialized bioreactors. As a result, these methods are typically not suited to field evaluation and can be time and labor intensive. Additionally, the reactors have a limited range of flow rates (from static to ~7 mL min$^{-1}$), hold a limited number of samples, and cannot easily be adapted for use with multi-species biofouling communities.

Optical biosensors have been employed to analyze biofouling formation. These techniques offer a high level of detail such that individual bacterial cells can be seen at high magnifications; however, the utility of optical images is often limited by a narrow field of view that cannot capture the heterogeneous and topologically diverse nature of bacterial biofouling. In addition, some techniques can reconstruct biomass distribution only for biofouling of a limited thickness and opacity.

At least some of the embodiments of the disclosure described below are directed to apparatus and methods for quantifying an amount of biological material upon a surface.

BRIEF DESCRIPTION OF THE DRAWINGS

Example embodiments of the disclosure are described below with reference to the following accompanying drawings.

FIG. 3 are images of raw and stained substrates over different periods of time of fouling.

FIGS. 4a-4c are illustrative representations of a standard photograph and the photograph following image processing operations according to one embodiment.

DETAILED DESCRIPTION OF THE DISCLOSURE

Figure 1:
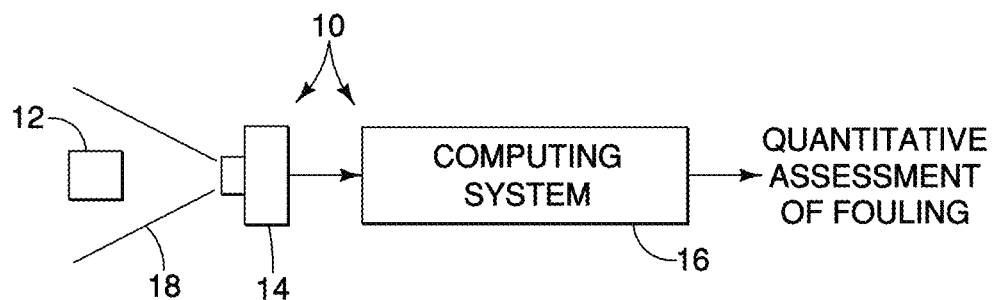
FIG. 1 is an illustrative representation of a biological material assessment system according to one embodiment.

This disclosure is submitted in furtherance of the constitutional purposes of the U.S. Patent Laws "to promote the progress of science and useful arts" (Article 1, Section 8).

At least some aspects of the disclosure are directed towards apparatus and methods for quantifying an amount of biological material or biofouling upon substrates. Some examples of biofouling which can be quantified include conditioning film, biological fouling, organic fouling, biofilms, fouling, microfouling, macrofouling, marine fouling, biomedical fouling, bioadhesion, underwater fouling, bioaccumulation, surface-associated biological material, and plaque.

Some embodiments enable the early stages of biofouling formation to be quantified. In addition, analysis assays described herein were able to discern subtle differences in surface fouling that accumulated over time. The entirety of a surface of a substrate can be assessed with just one image in some embodiments.

As described below, versatile photographic methods are presented in example embodiments to make the heterogeneous structure of biofouling more visible. For example, a broad-spectrum mixture of biomolecular stains may be applied to the surface of the substrate containing fouling of biological material to highlight primary and secondary metabolite components that make up the biofouling. Some combinations of dyes which may be used to stain major components of biofouling growing on sample surfaces are discussed below. The staining process was designed to enhance contrast of biofouling material from the substrate surface in digital photographs. Stain may be applied to both a region of the surface that has been fouled and to a section of the surface that was not exposed to the fouling conditions or has been cleaned, or to a separate but identical clean surface. Application of the stain(s) to the clean surface provides a background against which the fouled and stained region is compared. Both the fouled and clean surfaces are captured in a photograph in some embodiments and applying stain to a clean region may be used to confirm that the stain does not adhere to a surface when no biofouling is present. The stain may be applied to a surface with biofouling that has no clean region in some embodiments. In one embodiment, substrates may be imaged and processed to verify that a clean surface is actually clean, at least to within the limits of detection.

Thereafter, image data of digital photographs of the fouled surface may be generated and image analysis used to quantify the overall amount of biofouling growth visible in an image according to some of disclosed embodiments. In particular, a multilevel thresholding process may be used to process the data of the images of the fouled surface in at least one disclosed embodiment. At least some embodiments of the disclosure provide accurate quantification of the amount of fouling of biological material even when the images do not have significant separation of color or grayscale intensities between the foreground and background.

Some disclosed methods enable measurement of fouling over an entire area of a surface of interest in a straightforward manner, with a high degree of accuracy, and which are not confined to a laboratory. The disclosed methods may be useful for rapid analysis of biofouling formation and biofouling in biomedical, industrial, marine and other settings.

In addition, the resulting precision of the biofouling quantification assays described herein are similar to that of the more laborious means of measuring the optical density of suspended biofouling cultures. Some example methods and apparatus described herein may be used in field testing or other non-laboratory settings.

Referring to FIG. 1, an example biological material fouling assessment system 10 is shown according to one embodiment. The depicted system 10 includes an imaging system 14 and a computing system 16 which quantitatively assesses an amount of fouling present upon a surface of a substrate 12, such as a coupon, which is a representative sample of a material which may be used in a laboratory setting.

As described in detail below, substrate 12 may be exposed to an aqueous environment, for example, for a specified period of time. Thereafter, the substrate 12 may be analyzed using system 10 to quantify the amount of fouling which has occurred upon surfaces of the substrate 12. As described in some example embodiments below, the substrate 12 may be stained following the exposure of the substrate to the aqueous environment and prior to imaging of the surface of the substrate 12 by imaging system 14.

Imaging system 14 is configured to generate digital images of the substrate 12 including image data for a plurality of pixels. In one embodiment, imaging system 14 is a digital camera which is configured to generate color digital photographs of the substrate. Other configurations of imaging system 14 may be used in other embodiments.

Imaging system 14 configured as a digital camera includes an optical system, such as a lens and shutter, which exposes an image sensor, such as a charge-coupled device (CCD) or CMOS sensor, to light. The image sensor is configured to generate image data including digital values for a plurality of pixels of the image sensor which are indicative of the intensities of the light received by the respective pixels of the sensor. In some digital cameras, color photograph images may be generated, for example, by filtering light before being applied to image sensor, through use of multiple image sensors, through use of a Foveon X3 sensor, or by demosaicing in some illustrated embodiments. In color applications, intensity information may be provided for individual color channels (e.g., red, green, blue) for each pixel of the image sensor. In some embodiments, a color image may be converted to grayscale which serves as an overall average of intensity of the different colors and be used as a grayscale channel. The individual colors may differentiate features within the biofouling (by reducing bias from surface texture or contours and resulting shadowing) while the grayscale images serves as an overall average. Each of the individual color channels including grayscale may be separately processed to provide independent representations of the amount of fouling in some example embodiments discussed below.

The generated image data is stored in imaging system 14 and communicated to computing system 16 for processing and quantification of the fouling of the surface of substrate 12 in one embodiment. The use of a digital camera enables an entirety of a surface of substrate (e.g., 2.5 cm×2.5 cm coupon) to be imaged in a single photograph due to the relatively wide field of view of some digital cameras compared with other imaging arrangements. For example, some digital cameras provide a field of view of 10-1000 mm or larger. A user may also select less than the entirety of a surface of the substrate to be imaged in some embodiments. For example, an area slightly smaller than the whole substrate may be imaged to limit edge effects (i.e., the tendency of biofouling to accumulate at the edges) and related lens and chromatic aberrations that may occur during photography.

Imaging system 14 is utilized to generate images of the fouled surface of the substrate 12 which may or may not have been previously stained. In one imaging method, the substrate 12 is placed in a clean dish below imaging system 14 in the form of a digital camera (e.g., Panasonic DMC-L3) positioned with a stand. Lighting for the photographs was controlled using the overhead lights in a biosafety cabinet in order to be consistent for each set of substrates 12. Bright diffused lighting may be used in but one implementation to avoid shadows, glare, and reflections on the samples. In particular, LED lighting panels (LimoStudio model AGG1089) may be used in some embodiments to provide bright diffused lighting.

The camera was operated in manual mode with the following settings: f/2, 1/60 s exposure, ISO 400, 5 mm focal length and no flash. The photographs were recorded in RAW format for later processing by computing system 12. In some embodiment, the photographs may be provided in a compressed format, such as jpeg. In some embodiments a macro lens may be used in conjunction with the camera.

In some embodiments, uniform lighting is provided over the substrate during imaging. This allows for better comparison between different substrates and on different days. For example, 2 LimoStudio 500 watt equivalent 5500K temperature LED lights operated at 50% output were used in some cases to light biofouled substrates. The substrates were then photographed with a digital camera.

In some embodiments, a board is used to hold the substrates in a near vertical position for capturing images. The board may be black or white to provide blank contrast. The board may have markings to indicate details of the substrate and the scale of the substrate. In some embodiments, photography may be carried out in ambient conditions (i.e., with ambient indoor or outdoor lights).

The photography of the substrates may also be carried out in an enclosed environment where ambient light is excluded in some embodiments. For example, the substrates to be imaged may be placed in an enclosure, such as a box, and the lamps or bulbs which provide uniform lighting of the substrate and the imaging system may be integral to the enclosure. Furthermore, the enclosure is designed to accommodate imaging systems of different types (e.g., digital cameras, fluorescent imaging detectors, cell phone cameras, etc.) in some examples and the enclosure may be designed to maintain the imaging system at a selected working and focal distance. In some embodiments, the enclosure is configured so that substrates can be placed inside for imaging, or alternatively, the enclosure is configured to be pressed against a fouled surface (e.g., the hull of a ship).

At times it is desirable to measure the amount of biofouling that has accumulated on a substrate 12 having a dark surface (e.g., black, dark blue, etc.). Photographs of stains on dark substrates may be difficult to analyze. However, in some embodiments, fluorescent imaging techniques may be utilized to analyze these photographs. This may be done on dark substrates or on a fouled substrate of any color. Stain mixtures are used to enhance contrast in images as discussed in further detail below. For example, a stain mixture having a dye which has fluorescent emission (e.g., such as Rhodamine, acridine orange, SYBR green, Phloxime B, Trypan Blue) may be applied to the substrate 12 for use in fluorescent imaging to enhance the fluorescent emission from the substrate 12. In some instances, the biofouling may include material, such as algae, that is autofluorescent (e.g., chlorophyll, tryptophan), and fluorescent images of this biofouling may be generated as described below with or without use of stains.

In one example fluorescent imaging implementation, a fouled substrate which has been stained is placed in a light tight box (or other environment which excludes ambient light) which also includes an appropriate imaging system which may include a digital camera or other apparatus having a charge-coupled device (CCD) or CMOS sensor as discussed above. In addition, a light source emits light having a known wavelength inside the box to act as an excitation source to stimulate fluorescent emission from stained biofouling upon the surface of the substrate 12. Further, an optical filter may be provided in front of the imaging system and which is configured to remove wavelengths of light emitted from the light source so the light received by the imaging system corresponds only to the fluorescent emission from the biofouling. The selected range of wavelengths may encompass the peak fluorescent emission. The fluorescent images may be processed to quantify an amount of biofouling as discussed further below. Fluorescent imaging may be carried out in addition to the imaging described previously, or alternatively, only one imaging method may be used.

Figure 2:
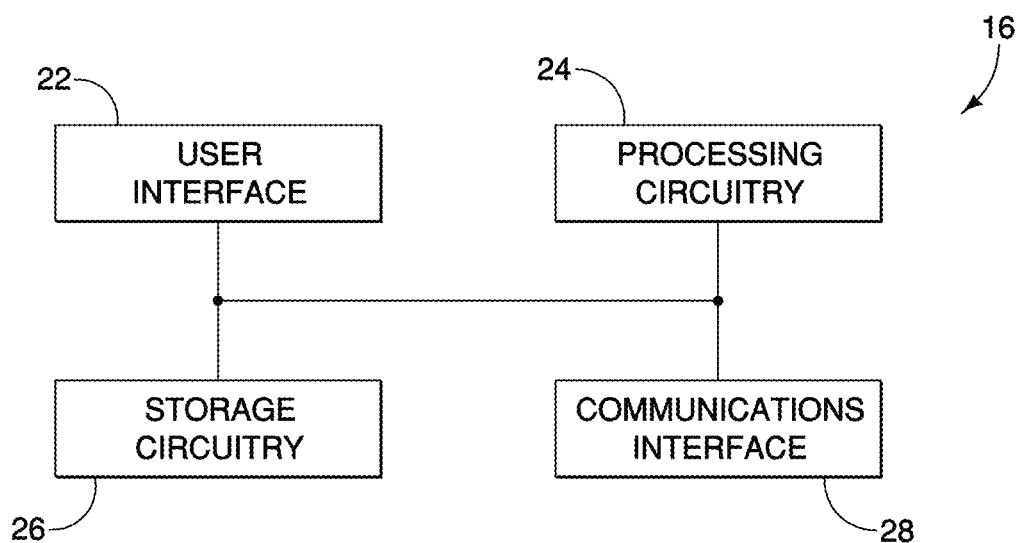
FIG. 2 is a functional block diagram of a computing system in one embodiment.

Referring to FIG. 2, one embodiment of computing system 16 is shown. In the illustrated example embodiment, computing system 16 includes a user interface 22, processing circuitry 24, storage circuitry 26, and a communications interface 28. Other embodiments of computing system 16 are possible including more, less and/or alternative components.

User interface 22 is configured to interact with a user including conveying data to a user (e.g., displaying visual images for observation by the user) as well as receiving inputs from the user. For example, a user may control operations of quantitative assessment of the fouling via user interface 22 and user interface 22 may be used to display results of the quantitative assessment of the fouling.

In one embodiment, processing circuitry 24 is arranged to process data, control data access and storage, issue commands, and control other desired operations. For example, processing circuitry 24 may implement image analysis operations to process intensity information of pixels of a photograph to provide information regarding an amount of biological material upon a substrate surface in some embodiments as described in further detail below.

Processing circuitry 24 may comprise circuitry configured to implement desired programming provided by appropriate computer-readable storage media in at least one embodiment. For example, the processing circuitry 24 may be implemented as one or more processor(s) and/or other structure configured to execute executable instructions including, for example, software and/or firmware instructions. Other example embodiments of processing circuitry 14 include hardware logic, PGA, FPGA, ASIC, state machines, and/or other structures alone or in combination with one or more processor(s). These examples of processing circuitry 24 are for illustration and other configurations are possible.

Storage circuitry 26 is configured to store programming such as executable code or instructions (e.g., software and/or firmware), electronic data, databases, image data (e.g., RGB and grayscale values for individual pixels of a digital image of substrate 12), or other digital information and may include computer-readable storage media. At least some embodiments or aspects described herein may be implemented using programming stored within one or more computer-readable storage medium of storage circuitry 26 and configured to control appropriate processing circuitry 24.

The computer-readable storage medium may be embodied in one or more articles of manufacture which can contain, store, or maintain programming, data and/or digital information for use by or in connection with an instruction execution system including processing circuitry 24 in one embodiment. For example, computer-readable storage media may be non-transitory and include any one of physical media such as electronic, magnetic, optical, electromagnetic, infrared or semiconductor media. Some more specific examples of computer-readable storage media include, but are not limited to, a portable magnetic computer diskette, such as a floppy diskette, a zip disk, a hard drive, random access memory, read only memory, flash memory, cache memory, and/or other configurations capable of storing programming, data, or other digital information.

Communications interface 28 is arranged to implement communications of computing system 16 with respect to external devices such as imaging system 14. For example, communications interface 28 may be arranged to communicate information bi-directionally with respect to computing system 16. In particular, communications interface 28 may receive image data of a plurality of images from imaging system 14. Communications interface 28 may be implemented as a network interface card (NIC), serial or parallel connection, USB port, Firewire interface, flash memory interface, or any other suitable arrangement for implementing communications with respect to computing system 16.

As mentioned above, processing circuitry 24 may be configured to perform image processing operations upon the image data of images of substrate 12 generated by imaging system 14 in one embodiment. In the described embodiment, the processing circuitry 24 is configured to separate the different color channels (e.g., red, blue, green) of the image data and to calculate grayscale values for the pixels as well. Thereafter, the processing circuitry 24 processes each individual color channel (including grayscale) separately and independently of the other color channels in one embodiment. Processing circuitry 24 generates quantitative information which is indicative of an amount fouling of biological material upon the surface of substrate 12 for each of the color channels in one embodiment. The quantification result for one of the color channels may be selected as being representative of the amount of fouling in one embodiment.

In some embodiments, substrates 12 in the form of square 2.5 cm by 2.5 cm coupons of FR4 fiberglass (McMaster-Carr, Los Angeles, Calif.) may be utilized for the fouling analysis. As mentioned previously, the surface of the substrate 12 may be stained in some embodiments to enhance the visibility of cells, nucleic acids and proteins that make up biofouling as well as for use with fluorescent imaging in some embodiments. Biomolecular stains selectively adhere to specific cellular or biological components and can also be used to enhance contrast and/or fluorescence.

Staining prior to image analysis increases the accuracy of biofouling growth measurements in some of the disclosed embodiments. Stain may assist with yielding an appreciable difference in color or grayscale intensity between the biological material and background.

In accordance with example implementations, a substrate to be analyzed can be exposed to a stain formulation that includes one or more dye formulas or formulations. The stain formulation is configured to bind with one or more of organic matter (e.g., protein, sugars, nucleic acids, lipids) and/or microorganisms that form the basis of biofilms which can be a precursor to biofouling. These stain formulations can adhere to or bond with biomolecules (e.g., proteins, phosphoproteins, phospholipids, nucleic acids, lipids, etc.) by adhering to a target biomolecule or to a class of biomolecules. The purpose of the stain is to highlight the target biomolecule in images (e.g., images acquired by microscopy). More than one stain may be used to highlight multiple components of a sample being analyzed.

The stain formulations may have one, two, or at least three components. Each component can be associated with specific bioorganic matter and each component can reflect a different UV-vis spectra than the other two. For example, one component may be selected to bind with proteins, phosphoproteins and/or phospholipids and when bound illuminate a red or pink color; another component may be used to bind with proteins as well and when bound illuminate blue color; and the third component may be selected to bind with nucleic acids and when bound may fluoresce red, violet, or purple. In accordance with example implementations, a stain mixture is provided that can include all three of the above components and stain bioorganic matter without noticeable negative impacts of interaction with one another.

In accordance with example implementations the method can include providing a stain that includes at least two components, the first of the two components binding with a first bioorganic material and exhibiting a first emission when bound, and the second of the two components binding with a second bioorganic material and exhibiting a second emission when bound. As an example, the first bioorganic material can be a protein and the first emission can be red, and the second bioorganic material can be a nucleic acid and the second emission can be fluorescent.

One of the components can be an organoiodine compound. This component may be red or pink. This component may be used to stain phosphoproteins, phospholipids and proteins. Example organoiodine compounds that can be utilized as part of this component of the stain formulation include, but are not limited to; erythrosine; red no. 3; disodium salt of 2,4,5,7-tetraiodofluorescein; 2-(6-Hydroxy-2,4,5,7-tetraiodo-3-oxo-xanthen-9-yl)benzoic acid, Erythrosine B; Erythrosin B; Acid Red 51; C.I. 45430; FD & C Red No. 3; E127; 2',4',5',7'-Tetraiodo-3',6'-dihydroxy-spiro [3H-isobenzofuran-1,9'-xanthen]-3-one disodium salt; Tetraiodofluorescein Sodium Salt; Calcoid Erythrosine N; 2,4, 5,7-Tetraiodo-3,6-dihydroxyxanthene-9-spiro-1'-3H-isobenzofuran-3'-one disodium salt; 2',4',5',7'-Tetraiodofluorescein, disodium salt; C.I. Food Red 14; Aizen Erythrosine; Tetraiodifluorescein, disodium salt; Spiro[isobenzofuran-1(3H),9'-[9H]xanthen]-3-one, 3',6'-dihydroxy-2',4',5',7'-tetraiodo-, disodium salt. This component may have the chemical formula $C_{20}H_6I_4Na_2O_5$. and may have the following chemical structure:

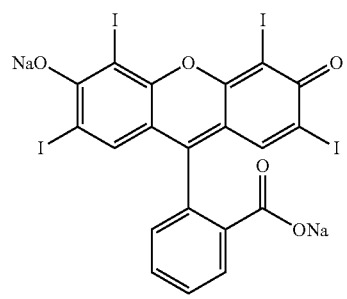

Another component of the stain formulation can be a triphenylmethane dye that can stain proteins and demonstrate blue color. An example triphenylmethane is a disulphonated triphenylmethane. This component can include but is not limited to: Coomassie® Brilliant Blue G-250; Colour Index 42655; C.I. Acid Blue 90; Brilliant indocyanine G; Brillantindocyanin G; Xylene Brilliant Cyanine G; or Serva Blue G. This component may have the chemical formula $C_{47}H_{50}N_3NaO_7S_2$ and may have the following chemical structure:

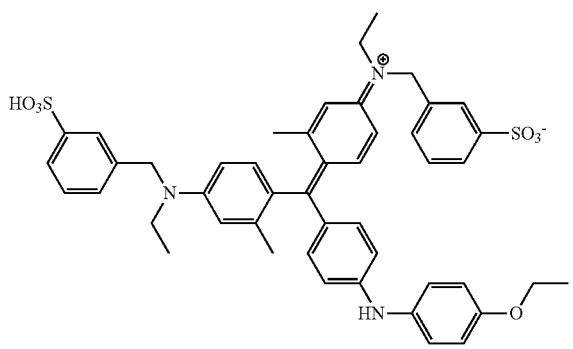

The third component of the stain formulation can be a fluorine dye such as a Rhodamine or derivative of same. This component can be configured to bind nucleic acids and when bound elicit fluorescence in a red violet or purple color. This component includes, but is not limited to Rhodamine B; Rhodamine 610; Colour Index Pigment Violet 1; Basic Violet 10; [9-(2-carboxyphenyl)-6-diethylamino-3-xanthenylidene]-diethylammonium chloride; or Colour Index 45170. This component can have the chemical formula $C_{28}H_{31}ClN_2O_3$ and the following chemical structure:

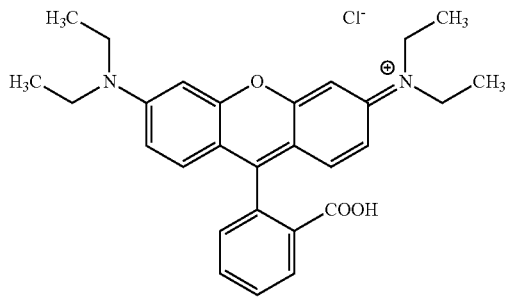 [SMILES: [Cl-] ; CCN(CC)c1ccc2c(-c3ccccc3C(=O)O)c3ccc(=[N+](CC)CC)cc-3oc2c1]

The stain mixture can be prepared from individual or multiple selected components. Each of the components can be provided neat or as part of a solution. The solution can be buffered to a predetermined pH.

For example all three components may be mixed in a suitable solvent (e.g., water, saline, buffered saline, phosphate buffered saline) with the solvent being used to dilute the components to a suitable concentration. The components may be mixed in a ratio organoiodine:triphenylmethane:Rhodamine of 1:3:2. The stains may be mixed by adding 0.1 grams of organoiodine, 0.3 grams triphenylmethane, and 0.2 grams Rhodamine to 100 milliliters of solvent. The solvent may be a 0.1 M solution of phosphate buffered saline. The stains may be made into a liquid solution with 0.1% (wt/wt) organoiodine, 0.3% (wt/wt) triphenylmethane, 0.2% (wt/wt) Rhodamine, and 99.4% solvent. The stains may be mixed as a concentrate wherein the percentage of organoiodine:triphenylmethane:Rhodamine is higher than 1.0% but where the ratio of the components is preserved. The percentage of organoiodine may vary from 0.05% to 1.0% (wt/wt). The percentage of triphenylmethane may vary from 0.05% to 1.0% (wt/wt). The percentage of Rhodamine may vary from 0.05% to 1.0% (wt/wt).

The stain formulation can be provided in the form of a dip wherein the substrate is at least partially engulfed in the formulation prior to analysis. The stain formulation may also be provided as a spray wherein the substrate, particularly in field analysis, is sprayed with the formulation prior to analysis.

The substrate can be prepared for staining by rinsing the substrate with an aqueous solution that may be buffered or non-buffered. The stain formulation can then be applied and analysis of the stained substrate can take place with the systems and/or according to the methods of the present disclosure.

Accordingly, in some embodiments, the stains are selected to target and attach to living organisms and other organic matter that is present as a result of biofouling. Usage of the example staining processes described herein resulted in digital images with color intensities which are representative of the amount of biofouling present.

In one example staining embodiment, the substrate 12 is retrieved from an aqueous solution after a predetermined amount of time and fully submerged for 1-2 seconds in a bath of phosphate-buffered saline (PBS) to remove unbound or unattached fouling material. Thereafter, a selected volume of a broad-spectrum mixture of biomolecular stains (e.g., 100 µL) is applied to the substrates 12 with a pipette over the full area of the surface of the substrate 12 in one example application method to highlight primary and secondary metabolite components that make up the biological material.

In some implementations, particular biomolecular dyes were selected to highlight several components of surface-attached biomass. One example stain mixture which may be utilized contains erythrosine B (available from Thermo Fisher Scientific, Waltham, Mass.), Rhodamine (available from Keystone Analine Corporation, Chicago, Ill.), and Coomassie Brilliant Blue (available from Thermo Fisher Scientific). Erythrosine B is a cherry pink organoiodine compound that adheres to phosphoproteins and phospholipids and is used to identify microorganisms, rhodamine is a xanthene dye used to detect nucleic acids, and Coomassie Brilliant Blue G-250 is a triphenylmethane dye used to stain proteins. This example group of stains broadly attached to biomass without staining the underlying substrate. The use of a mixture of different stains resulted in increased enhancement of contrast compared with use of individual stains.

A more specific example of a stain mixture which may be utilized contains 100 mL of 0.1M concentration phosphate-buffered saline (PBS) at pH 7.4 with 0.1 g of erythrosine B, 0.2 g Key Acid Rhodamine WT, and 0.3 g Coomassie Brilliant Blue G-250 mixed in. An example PBS 1× concentration includes NaCl (8 g $L^{-1}$), KCL (0.2 g $L^{-1}$), $Na_2HPO_4$ (1.44 g $L^{-1}$), and $KH_2PO_4$ (0.24 g $L^{-1}$) with each component available from Thermo Fisher Scientific. The substrate 12 may be submerged gently at least once in PBS again for 1-2 seconds to remove excess stain.

The example stains and stain mixtures described herein are merely example stains which may be used. Other stains and stain mixtures may be selected and used to quantify other types of biofouling. In example embodiments, the stains may be applied by pipette or by dipping the substrates 12. Other application techniques may be utilized, such as spraying which enables field testing of environmental biofouling on man-made marine structures and vessels.

Referring to FIG. 3, photographs of three raw (unstained) and three stained substrates are shown at different time points 0, 48 and 144 hours. Differences in fouling on each substrate are subtle in the raw images while substrates that were stained show an obvious increase in fouling over time. In particular, although biofouling growth was expected to increase with time, differences in the raw photographs of the unstained substrate are very subtle, and the substrate exposed for 48 and 144 hours are only slightly darker than the original substrate. The slight change in the images over time appears uniformly distributed over the area of the substrate.

As seen in the second row of FIG. 3, staining has enhanced visibility and contrast of biofouling growth with respect to the substrate and across the area of each substrate and between the different time points. The biofouling is non-uniform and the increase in biofouling growth from 0 to 144 hours is apparent.

As mentioned above, processing circuitry 24 may perform image analysis upon the images of the substrate which are stained or not stained. In some embodiments, the images are in color and processing circuitry 24 may separate the individual red, blue, and green color channels of a jpeg image in one embodiment. A grayscale channel may also be calculated and processing circuitry 24 may thereafter perform the processing described below with respect to FIGS. 5a-5d for each color including grayscale. Analysis of the color channels was used to accurately identify biomass as opposed to shadowing due to the texture of the coupon or the biofouling.

Stained substrates appear darkest wherever the biofouling is thickest and most developed. Therefore, color intensity can serve as the basis for quantitative image analysis in some embodiments described herein. As described in detail below, one embodiment of the image analysis uses a multilevel thresholding technique to delineate foreground (biological material) from background (clean) and to rapidly measure biofouling in digital photographs.

In particular, in one image analysis embodiment, the biological material upon the surface of the substrate is evaluated on each substrate to determine the amount of biological material present and which may be represented as a biofouling growth intensity (BGI) value between 0 and 100 that represents an absolute score for biofouling growth intensity over the entire substrate surface or any selected area of the substrate surface. Measuring biofouling growth intensity allows direct and quantifiable comparison of biofouling growth on different substrates. The determined biofouling growth intensity provides a measure of areal coverage of the biofouling as well as accounts for density and thickness of surface growth. A BGI value may be calculated for each color channel (if color images are used) and independently indicative of the amount of biofouling.

One embodiment of an image analysis method is described below with respect to FIGS. 4a-4c and FIGS. 5a-5d. As mentioned above, a multilevel thresholding technique is utilized in one specific embodiment. FIGS. 4a-4c are a series of representations of a standard photograph (which does not include biofouling) which is used as a representative example to demonstrate some image processing operations which may be used because it has elements that are easy to distinguish (separation of the dark cars from the ground) and elements that are difficult to distinguish such as the difference between the ground and plants. FIGS. 5a-5d are histograms of frequencies of each grayscale intensity level for the grayscale channel for the different representations of FIGS. 4a-4c as described further below. The grayscale channel is an overall average of the individual color channels.

Figure 5A:
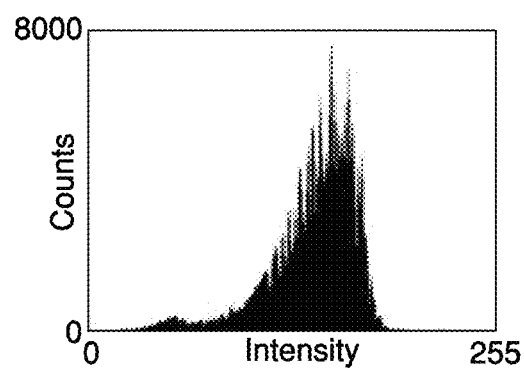
FIGS. 5a-5d are histograms of frequencies for the grayscale channel for the different illustrative representations shown in FIGS. 4a-4c.

FIG. 4a shows the standard grayscale image and FIG. 5a shows the corresponding histogram of the frequencies of each grayscale intensity level. The histogram has a strongly uneven bimodal distribution. The image is processed using one example biofouling growth intensity analysis method described below to separate high-contrast signal from background.

Figure 5B:
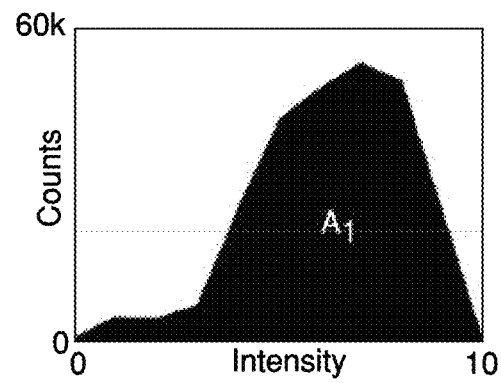

FIG. 4b shows the image resulting from processing (and FIG. 5b shows the corresponding histogram) including the application of a multilevel threshold to the image. In particular, the values of the intensity for the grayscale channel of the pixels are used to associate the pixels of the image with a plurality of bins or groups (e.g., N=10 defined by 11 thresholds) which correspond to a plurality of different intensity value ranges in the presently described example.

For example, a given pixel is assigned by the processing circuitry 24 to a given bin if the intensity value of the given pixel falls between upper and lower intensity thresholds of the given bin. The purpose of the multilevel threshold is to enhance visibility of the full spectrum of biofouling growth. The histogram of FIG. 5b is simplified, stretched and has enhanced contrast compared with the histogram of FIG. 5a. The threshold levels can be determined in multiple ways, for example, including recursive optimization as described in Arora S, Acharya J, Verma A, Panigrahi P K; *Multilevel thresholding for image segmentation through a fast statistical recursive algorithm*, Pattern Recogn Lett 29(2):119-125 (2008); Huang D-Y, Wang C-H Optimal multi-level thresholding using a two-stage Otsu optimization approach, Pattern Recogn Lett 30(3):275-284 (2009); Liao P-S, Chen T-S, Chung P-C, *A fast algorithm for multilevel thresholding*, J Inf Sci Eng 17(5):713-727 (2001); and Sri Madhava Raja N, Rajinikanth V, Latha K, *Otsu based optimal multilevel image thresholding using firefly algorithm*, Modell Simul Eng 2014:17 (2014), the teachings of which are incorporated herein by reference.

Figure 5C:
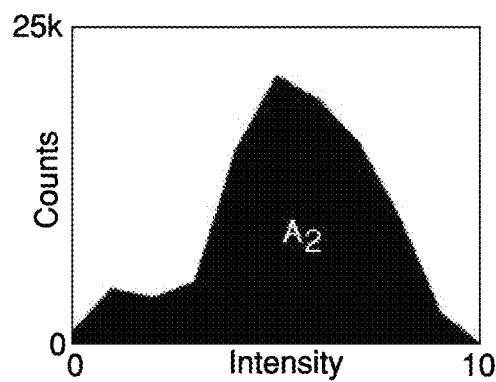

FIG. 4c shows the image resulting from processing (and FIG. 5c shows the corresponding histogram) including the application of a filter to the histogram of FIG. 5b. In one embodiment, a ramp filter is used which enhances the relative importance of high-intensity (i.e., dark) values in the data set (FIG. 4c) compared with low-intensity values. For example, the ramp filter weights the numbers of the pixels for the bins which correspond to the intensity value ranges of higher intensities an increased amount compared with the weighting of the numbers of the pixels for the bins which correspond to the intensity value ranges of lower intensities.

In one more specific example, a simple linear ramp function is used where pixels in the first group (including the pixels with the lowest intensity values) were multiplied by 0, the second group by $1/11$, the third group by $2/11$, and so on, with the last group (including the pixels with the highest intensity values) being multiplied by 1. The use of a linear ramp filter in one embodiment does not artificially introduce a non-linear trend. Further, the filtered histograms of substrates 12 with thick biofouling are not significantly changed by the ramp filter; on the other hand, the histograms from relatively clean substrates 12 are heavily filtered. The numbers of pixels in the individual bins before the application of the ramp filter may be referred to as initial numbers and the numbers of pixels in the individual bins after the application of the ramp filter may be referred to as modified numbers.

As mentioned above, fluorescent imaging may be used to generate images of the substrate in some embodiments. The ramp filter may be inverted with respect to the above-described ramp filter if fluorescent imaging is used where low intensity pixels are weighted an increased amount compared high intensity pixels.

Figure 5D:
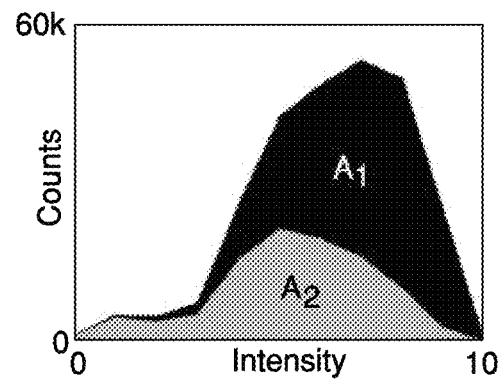

Referring to FIG. 5d, the data of the histograms of FIGS. 5b and 5c is used in one embodiment to determine the amount of fouling of biological material upon the substrate surface (e.g., determine a biofouling growth intensity value). For example, the area under the filtered histogram (FIG. 5c) is compared to the area of the thresholded histogram (FIG. 5b) to measure how dark or light the image is overall and, thus, how much biofouling it has in one embodiment.

In one more specific example embodiment, the processing circuitry is configured to divide a total or sum of the number of the pixels for the bins after the application of the ramp filter (i.e., the modified numbers of the pixels) by a total or sum of the number of the pixels for the bins prior to the application of the ramp filter (i.e., the initial numbers of the pixels) to generate the information which is indicative of the amount of the fouling of the biological material upon the surface of the substrate.

For example, the area under the filtered histogram ($A_2$) corresponding to the sum of the pixels of the histogram of FIG. 5c is divided by the area under the original histogram ($A_1$) corresponding to the sum of the pixels of the histogram of FIG. 5b and the result of the division is multiplied by 100 to provide the amount of biological material fouling (total biomass) on the substrate surface as a percentage. The resultant value may be referred to as the biofouling growth intensity.

The above-described example image processing distinguishes high-contrast objects and medium-contrast objects from the background or surface of the substrate. The relative importance of high-contrast objects (which in this example could represent macrofouling) is reflected in the calculation of the final biofouling growth intensity value and low-contrast features (e.g., representing microfouling) are weighted less in the described example. The image shown in FIG. 4c created by the biofouling growth intensity algorithm retains greater fidelity to the original image.

Biofouling growth intensity is not intended to measure the percent of area covered by biofouling. Rather, a biofouling growth intensity value of 100 represents an image with 100% of pixel intensity values in the darkest threshold group. Likewise, biofouling growth intensity of 0 would be made up of pixels only in the brightest group.

Figure 6:
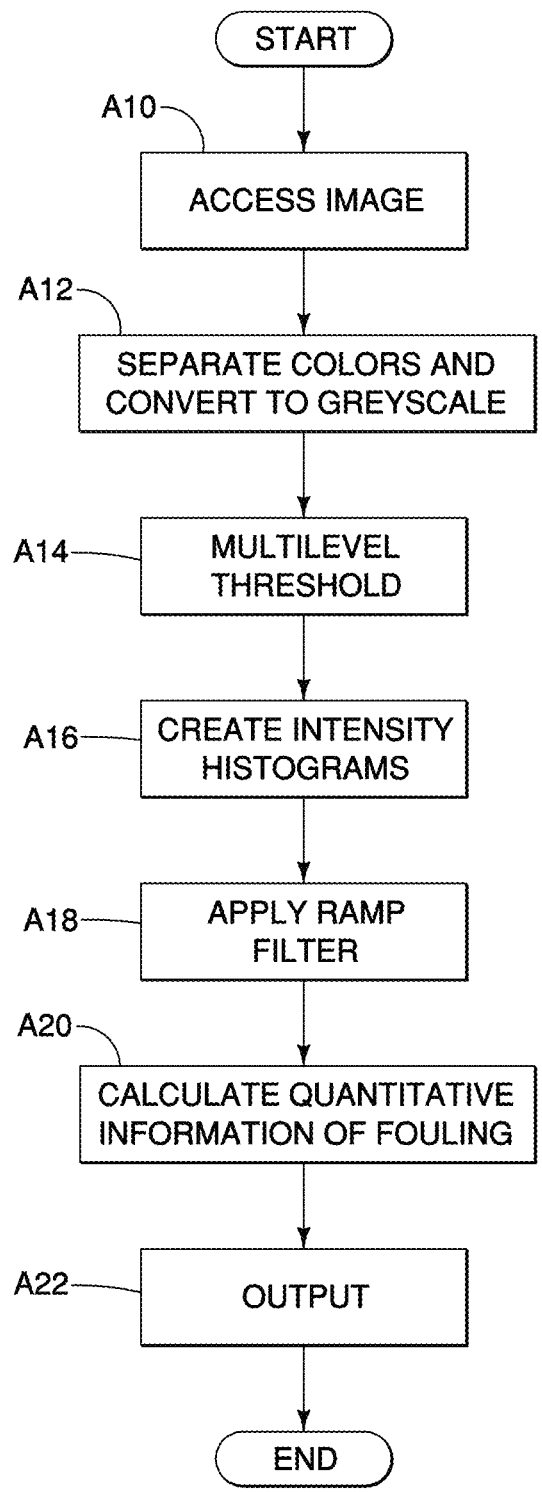
FIG. 6 is a flow chart of an image analysis method for quantifying an amount of biofouling according to one embodiment.

Referring to FIG. 6, an image analysis method is shown according to one embodiment. The depicted method may be used to quantify an amount of biofouling present upon a substrate and be performed by the processing circuitry in one example implementation. Other embodiments are possible including more, less and/or alternative acts.

At an act A10, an image of a substrate with biofouling present is accessed. In one embodiment, the accessed image is a compressed jpeg image although images of other formats may be used.

At an act A12, color information within the image is separated into respective color channels (e.g., red, blue, green) and converted to grayscale by averaging intensity values from each color channel. Thereafter, the individual color channels (e.g., red, blue, green, grayscale) are processed independently from one another in the subsequent acts.

At an act A14, a multilevel threshold is applied to the data of each of the color channels which associates the pixels of the respective color channel with different bins corresponding to the intensity values of the pixels and the intensity value ranges of the bins.

At an act A16, an intensity histogram is generated for each of the color channels using the results of act A14 for the respective color channel.

At an act A18, a ramp filter is applied to the results of act A14 to weight different bins (corresponding to different intensities) differently for each of the color channels. For example, if a digital camera was used to acquire the images, the bins corresponding to increased intensities are weighted an increased amount compared to bins corresponding to decreased intensities. If fluorescent imaging is used, the bins corresponding to increased intensities are weighted a decreased amount compared to bins corresponding to decreased intensities.

At an act A20, quantitative information regarding an amount of fouling present upon the substrate is determined for each of the color channels. In one method, the sum of the pixels in act A18 (i.e., after the weighting) is divided by the sum of the pixels in act A14 (i.e., before the weighting) to determine the quantitative information.

At an act A22, the quantitative information regarding the amount of fouling present for each of the color channels is outputted, stored, displayed, etc. Other information may also be provided, such as enhanced images of the fouling using the data resulting from act A18 described above.

Although the above-described method is described being performed independently for each of the color channels, the method may also be performed for only one of the color channels and the resultant information used to quantify the amount of fouling present in other embodiments.

Figure 7:
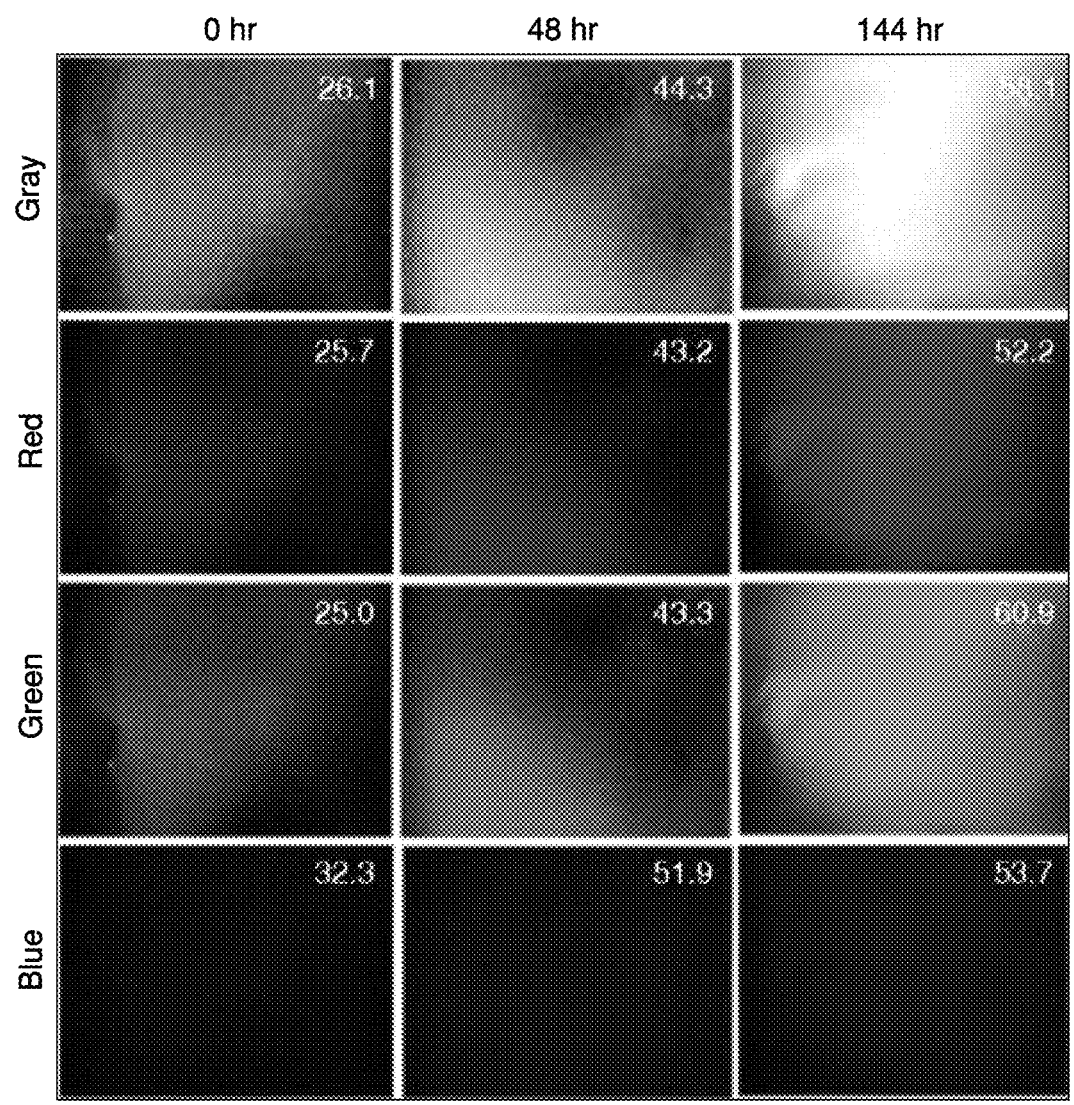
FIG. 7 are images created during biofouling growth intensity analysis of the substrates shown in FIG. 3.

Referring to FIG. 7, example images created during biofouling growth intensity analysis of the stained of substrates of FIG. 3 are shown. The example image analysis method described above with respect to FIGS. 4a-4c and FIGS. 5a-5d was used to analyze the grayscale image as well as each of the three color channels (e.g., red, blue, green) of an image. The image analysis was performed at different moments in time corresponding to 0, 48 and 144 hours of exposure to an aqueous solution. The biofouling growth intensity values for each of the color channels and time points are also shown.

Clear changes in the color intensity can be seen as biofouling accumulates and grows over time. Each color shows an increase in biofouling growth from 0 to 144 hours and the gray and green channels appear to retain finer detail in the image and have distinct biofouling growth intensity values. For example, blue and red images appear saturated at 144 hours while gray and green images more clearly show the distinct macroscopic morphology of the biofouling. The described image analysis extracted quantified values of biofouling growth from visually observable trends seen in FIG. 7. These images may be readily visually inspected to provide a platform for further unbiased quantification. Depending upon applications of use, different ones of the color channels may be used to quantify the accumulation of biological material.

Referring to FIGS. 8a-8d, comparisons of biofouling growth intensity values to cell density (measured by optical density) over time for each of the color channels of a digital photograph are shown. The biofouling growth intensity values are shown on a linear scale (left in the figures) and measured cell density is shown on a log scale (right in the figures). Error bars show standard deviation from three independent samples in all cases.

Figure 8A:
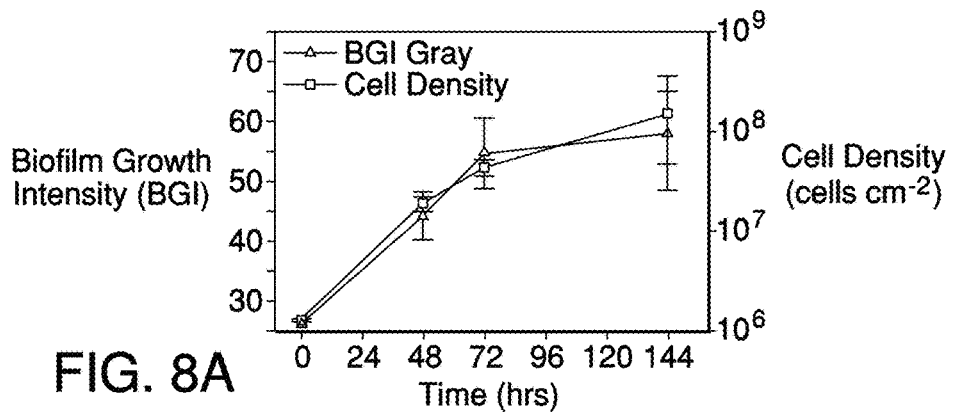
FIGS. 8a-8d are graphical representations of biofouling growth intensity values to cell density measured over time.
Figure 8B:
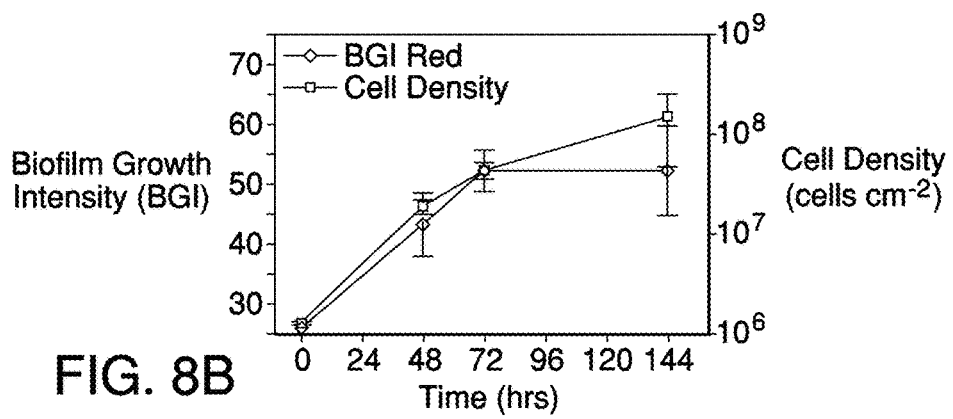
Figure 8C:
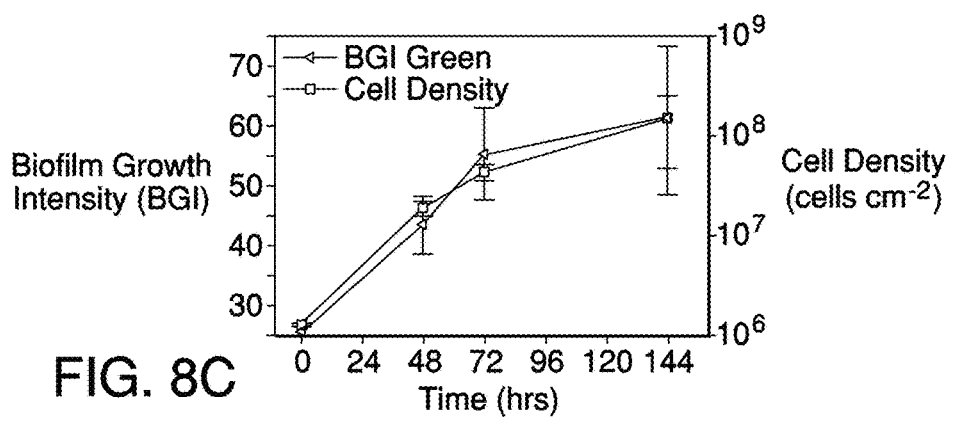
Figure 8D:
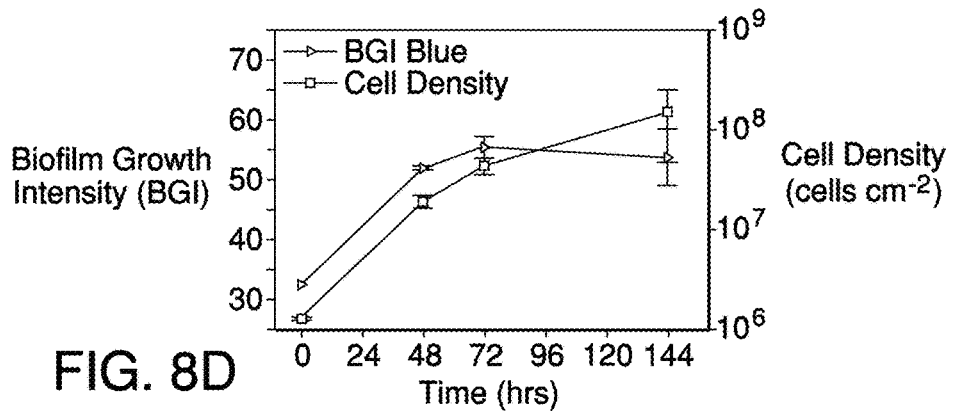

As shown, the biofouling growth intensity values match the trend observed for cell density on the surface. FIGS. 8a-8d show well-matched data from grayscale, red, green, and blue channels, respectively, of full-color digital photographs. In addition, the biofouling growth intensity values measured from a grayscale image and from the green channel (FIGS. 8a and 8c) appear to fit better than data from the red and blue channels (FIGS. 8b and 8d).

It is noted that the rise in biofouling growth intensity leveled off in the red and blue channels after 72 hours likely because those color channels were saturated more quickly by the purple-hued stain. An increase in biofouling growth intensity by approximately 15 corresponds to a 1 log increase in cell density on the surface. The standard deviation of biofouling growth intensity measurements from triplicate sample substrates was approximately 5 (though this increases with the magnitude of the measurement). Accordingly, the biofouling growth intensity according to the example embodiment described above accurately predicted cell density to within ~⅓ of a logarithmic unit change in cell density, which is approximately the same precision as an optical density method of measuring biofouling growth.

The discussion below proceeds with respect to an example fouling process used to create the substrates which were used to obtain the results shown in FIGS. 8a-8d. The substrates were initially exposed to a liquid culture of *Pseudomonas putida* (ATCC 39169) bacteria. The substrates were placed in petri dishes with 25 mL tryptic soy broth (available from BD Biosciences, San Jose, Calif.). Each dish had two coupons, one for staining and image analysis and one for cell density measurements. The dishes were inoculated with 100 μL *P. putida* and left covered in static and ambient conditions (~20° C.) for up to 6 days (144 hours). Additional tryptic soy broth (TSB) was added after 2 days to prevent dehydration of the remaining samples.

The fouled substrates were then stained, photographed, and analyzed using the image analysis method shown in FIG. 6. In parallel, identical substrates were analyzed by a standard method where cell density of the biofouling was measured after removing the cells by sonication and dispersing them in solution. The analysis was performed at four time points in this example (0, 48, 72, and 144 hours).

The following provides additional details regarding quantifying the amount of biofouling used to calculate cell density (i.e., the control) in FIGS. 8a-8d. After undergoing a staining procedure using PBS in place of stain, triplicate substrates for each time point were placed in conical 50-mL centrifuge tubes and 15 mL of PBS with 0.05% Tween 20 (available from Sigma-Aldrich) was added to each tube (i.e., enough to fully cover the sample). The sample tubes were placed in a sonicating bath filled with water for 30 min to remove biofouling from the surface and disperse it into the buffered saline. After sonication, the biofouling was further dispersed with a vortex mixer prior to analysis. Three 1-mL samples were pipetted from each test tube into disposable spectroscopy cuvettes. The optical density at 600 nm ($OD_{600}$) was measured for each substrate 12 using a UV-visible spectroscopy system (Model 8453 available from Agilent Technologies, Inc.). Optical density was chosen over viable cell count as it provides a more accurate measure of the total number of cells (live, dead, and non-culturable) and also takes into account cell size (i.e., that large cells have a greater contribution to optical density and to biomass on the surface of a sample). Optical density was measured in absorbance units (AU) and compared to a reference sample with PBS and Tween 20 but no bacteria. In the range 0-1 AU, optical density is roughly proportional to cell density with $3.9 \times 10^8$ cells $mL^{-1}$ per unit AU. This relation was used to calculate the number of cells dispersed in the solution (cells $mL^{-1}$) and that was converted to areal density (cells $cm^{-2}$) of biofouling on the surface of the substrate (counted as both sides of a 2.5- by 2.5-cm substrate, excluding edges). Areal cell density was used as a control against which the image analysis methods discussed above was compared.

Figure 9:
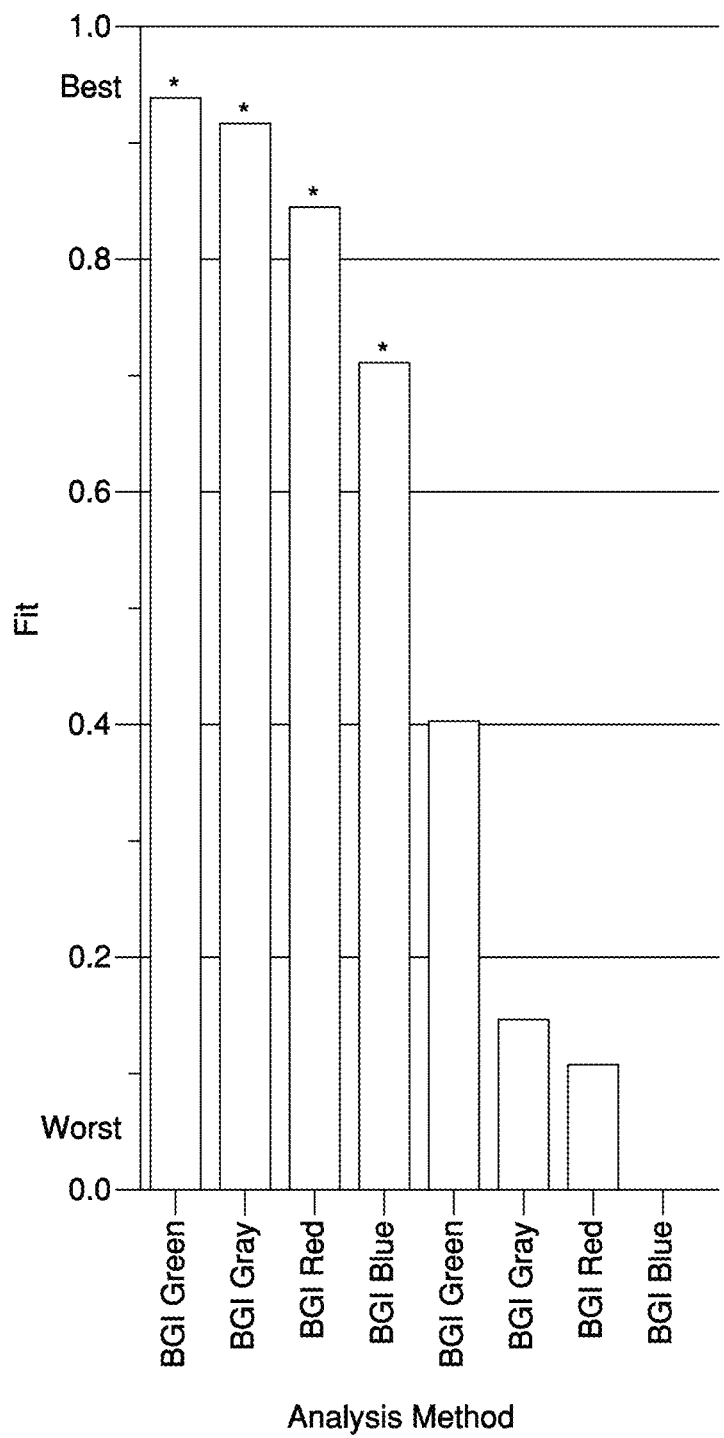
FIG. 9 is a graphical representation of calculated biofouling growth intensity values using different color channels.

Referring to FIG. 9, the results for the image analysis methods for each of the color channels with and without staining are shown from best to worst fit with independently measured cell density. Image analysis algorithms applied to substrates that were stained are indicated by a star (*). The illustrated graphical bars correspond to the color channels analyzed (red, green, and blue) with gray indicating a grayscale version of the full-color image. Samples that were not stained showed poor fit with optical density data compared with samples that were stained.

As shown, the multilevel thresholding analysis of green, gray, and red data were the three highest ranked methods of analysis. The multilevel thresholding process correlated well primarily because the process accurately quantified a broader range of biofouling growth from initiation (when no bacteria was present) to maturity (when the stained biofouling was dark and widespread). In addition, staining of substrates uniformly improved fit of image analysis data as shown with the top four analyses benefiting from enhanced contrast in images with staining.

In some embodiments, a color of the substrate may be used to select which particular color channel is used to quantify the amount of fouling. For example, if a blue substrate is used, the other color channels, such as red, green or grayscale, may provide increased contrast of fouling with respect to the substrate and be used to quantify the amount of biofouling present.

Figure 10A:
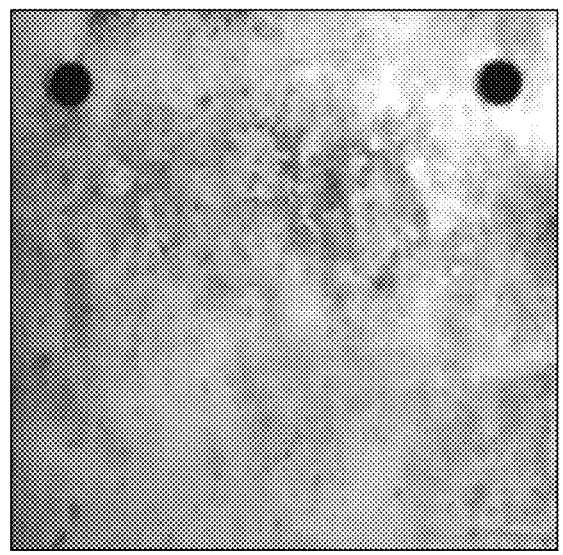
FIGS. 10a and 10b are images resulting from the use of fluorescent imaging of a fouled substrate.

As mentioned above, fluorescent imaging may be used to generate images to be processed as discussed previously. Referring to FIG. 10a, an example fluorescent image of a sample with biofouling is shown and fluorescent emission from the stained fouling is used to determine the amount of fouling (brighter is more fouled).

Figure 10B:
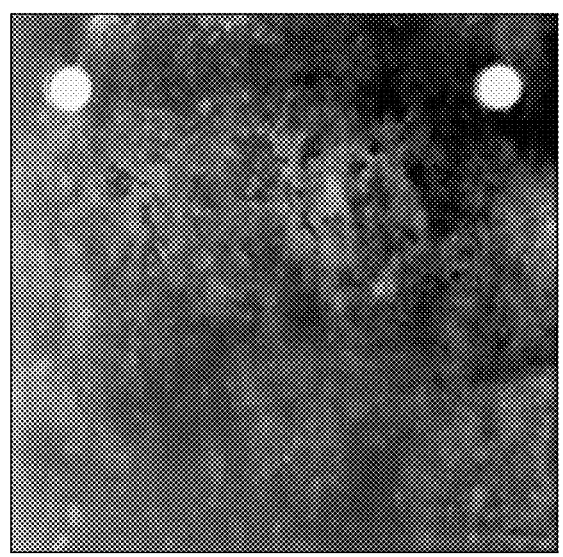

Referring to FIG. 10b, the fluorescent image can be inverted prior to analysis if desired. Inverting the intensity levels makes the fouling appear dark (i.e., high intensity pixels are converted to a corresponding low intensity value and vice versa). This gives the image the characteristics of other non-fluorescent color photographs of biofouling. If the convention utilized is for fouling to be dark, then the above-described ramp filter may weight pixels of increased intensity more than pixels of decreased intensity. If the convention utilized is for fouling to be light, then the above-described ramp filter may weight pixels of decreased intensity more than pixels of increased intensity. In some embodiments, the grayscale channel of the fluorescent image is used for image analysis to quantify the amount of fouling.

In one example application, the determined amount of fouling of biological material may be utilized to analyze the performance of anti-fouling paint upon surfaces, however the methods and apparatus of the disclosure may be utilized in any application where it is desired to quantify an amount of fouling present.

In example implementations, MATLAB® software packages were written to compile the multistep biofouling growth intensity analysis process. One of these packages is shown below in Appendix A which allows processing of a single image. An Appendix B which allows processing of multiple images is shown in the ASCII text file which is incorporated by reference above.

The software package of Appendix A prompts the user to select a sample image to import. Thereafter, the user selects an area of each substrate to be analyzed that does not include markings, any holes used to secure substrates, or substrate edges.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended aspects appropriately interpreted in accordance with the doctrine of equivalents.

Further, aspects herein have been presented for guidance in construction and/or operation of illustrative embodiments of the disclosure. Applicant(s) hereof consider these described illustrative embodiments to also include, disclose and describe further inventive aspects in addition to those explicitly disclosed. For example, the additional inventive aspects may include less, more and/or alternative features than those described in the illustrative embodiments. In more specific examples, Applicants consider the disclosure to include, disclose and describe methods which include less, more and/or alternative steps than those methods explicitly disclosed as well as apparatus which includes less, more and/or alternative structure than the explicitly disclosed structure.

---

APPENDIX A

```
% BGI: measures Biofilm growth intensity from an image
% Written by Curtis Larimer
function BGIsingle
close all
clear all
fName3 = 'Biofilm Image Data.xls';
% fName3 = uigetfile('*.xls','Select data file');
Samplenumcolm = xlsread(fName3,'A:A');
if isempty(Samplenumcolm) == 1
   SampleNum = 0;
else
SampleNum = max(Samplenumcolm);
end
[fName, Pathname] = uigetfile('*.jpg','Select a biofilm image');
Fullpath = strcat(Pathname,fName);
cd(Pathname);
BGIcallable(fName, Fullpath)
End
```

---

What is claimed is:

1. A biological material fouling assessment system comprising:
   processing circuitry configured to access image data of an image of a surface of a substrate which has been fouled with biological material;
   wherein the image data comprises intensity information regarding a plurality of pixels of the image;
   wherein the processing circuitry is further configured to process the intensity information regarding the pixels of the image to generate information which is indicative of an amount of the fouling of the biological material upon the surface of the substrate; and
   wherein the processing circuitry is further configured to compare the intensity information of the pixels before and after an application of a filter to generate the information which is indicative of the amount of the fouling of the biological material upon the surface of the substrate.

2. The system of claim 1 wherein the image is a color image and the processing circuitry is configured to process the intensity information including separating the pixels into respective ones of a plurality of different color channels according to the colors of the pixels, and wherein the processing circuitry is configured to process the pixels for the different color channels separately to generate the information which is indicative of the amount of the fouling comprising a value for each of the color channels which is indicative of the amount of the fouling of the biological material upon the surface of the substrate.

3. The system of claim 1 wherein the processing circuitry is configured to process the intensity information including using the intensity information to assign the pixels to a plurality of different bins which correspond to respective ones of a plurality of different intensity value ranges and use numbers of the pixels for the bins after the assigning to generate the information which is indicative of the amount of the fouling of the biological material upon the surface of the substrate.

4. The system of claim 3 wherein the processing circuitry is configured to further process the intensity information including applying the filter to the numbers of the pixels for the bins which weights the numbers of the pixels for the bins which correspond to the intensity value ranges of higher intensities an increased amount compared with the numbers of the pixels for the bins which correspond to the intensity value ranges of lower intensities.

5. The system of claim 4 wherein the processing circuitry is configured to divide a total number of the pixels for the bins after the application of the filter by a total number of the pixels for the bins prior to the application of the filter to generate the information which is indicative of the amount of the fouling of the biological material upon the surface of the substrate.

6. The system of claim 4 wherein the filter is a ramp filter.

7. The system of claim 1 wherein the generated information is indicative of the amount of the fouling of the biological material upon at least substantially an entirety of the surface of the substrate.

8. The system of claim 1 wherein the processing circuitry is configured to process the intensity information regarding at least substantially all of the pixels of the image to generate the information which is indicative of the amount of the fouling of the biological material upon the surface of the substrate.

9. The system of claim 1 wherein the processing circuitry is configured to process the intensity information regarding at least substantially all of the pixels of the image to generate the information which is indicative of the amount of the fouling of the biological material upon the surface of the substrate, and the generated information is calculated using the intensity information of the at least substantially all of the pixels of the image.

10. The system of claim 1 wherein the processing circuitry is configured to apply the filter to the intensity information of the pixels.

11. The system of claim 10 wherein the filter weights the intensity information of the pixels having relatively high-intensity values an increased amount compared with weighting by the filter of the intensity information of the pixels having relatively low-intensity values.

12. A biological material fouling assessment method comprising:

applying a stain to a surface of a substrate which has been fouled with biological material;

after the applying the stain, generating an image of the surface of the substrate including intensity information;

processing the intensity information of the image; and using the processing, generating information which is indicative of an amount of the fouling of the biological material upon the surface of the substrate by using a biofouling growth intensity analysis method that separates a high-contrast signal from the surface of the substrate.

13. The method of claim 12 wherein the generating the image comprises generating a digital photograph of at least substantially an entirety of the surface of the substrate in a single exposure using a digital camera.

14. The method of claim 12 wherein the processing comprises separating the intensity information into a plurality of different color channels and processing the intensity information for each of the different color channels separately to generate the information comprising a value for each of the respective color channels and which is indicative of the amount of the fouling of the biological material upon the surface of the substrate.

15. The method of claim 14 further comprising, using a color of the surface of the substrate, selecting the value for one of the color channels as being indicative of the amount of the fouling of the biological material upon the surface of the substrate.

16. The method of claim 12 wherein the intensity information comprises intensity values for a plurality of different pixels of the image and the processing comprises using the intensity values to assign the pixels to a plurality of different bins which correspond to respective ones of a plurality different intensity value ranges, and wherein the generating comprises generating the information using numbers of the pixels for the bins.

17. The method of claim 16 wherein the processing further comprises weighting the numbers of the pixels for bins which correspond to higher intensities more than the numbers of the pixels for bins which correspond to lower intensities.

18. The method of claim 17 wherein the generating the information comprises dividing a total number of the pixels after the weighting by a total number of the pixels prior to the weighting.

19. The method of claim 12 wherein the stain is fluorescent, and the generating the image comprises generating the image of fluorescent emission from the surface of the substrate.

20. The method of claim 12 wherein the stain comprises at least two components, the first of the two components binding with a first bioorganic material and exhibiting a first emission when bound and the second of the two components binding with a second bioorganic material and exhibiting a second emission when bound.

21. The method of claim 20 wherein the first bioorganic material is a protein and the first emission is red, and the second bioorganic material is a nucleic acid and the second emission is fluorescent.

22. The method of claim 12 wherein the processing comprises processing the intensity information regarding at least substantially all of a plurality of pixels of the image to generate the information which is indicative of the amount of the fouling of the biological material upon the surface of the substrate, and the generated information is calculated using the intensity information of the at least substantially all of the pixels of the image.

23. A biological material fouling assessment method comprising:

accessing image data of an image of a surface of a substrate which has been fouled with biological material, wherein the image data comprises intensity information for a plurality of different pixels of the image;

using the intensity information for the pixels, assigning the pixels into a plurality of different bins which correspond to respective ones of a plurality of different intensity value ranges, wherein the assigning provides different initial numbers of the pixels for different ones of the bins;

applying different weights to the initial numbers of the pixels for the different ones of the bins, wherein the applying results in a plurality of modified numbers of the pixels for the different ones of the bins; and generating information which is indicative of an amount of the fouling of the biological material upon the surface of the substrate by comparing the initial numbers and the modified numbers.

24. The method of claim 23 wherein the applying comprises applying increased weights to the initial numbers of the pixels for the bins which correspond to the intensity value ranges of higher intensities compared with the weights which are applied to the initial numbers of the pixels for the bins which correspond to the intensity value ranges of lower intensities.

25. The method of claim 23 wherein the image is a color image, and before the assigning, further comprising separating the pixels into a plurality of different color channels which correspond to the colors of the pixels, and wherein the assigning, the applying and the generating are performed independently for each of the color channels to generate the information which is indicative of the amount of the fouling of the biological material upon the surface of the substrate for each of the color channels.

26. An article of manufacture comprising non-transitory storage media storing programming which causes processing circuitry to perform the accessing, the assigning, the applying and the generating of claim 23.

27. A computing system configured to perform the accessing, the assigning, the applying and the generating of claim 23.

28. The method of claim 23 wherein the generating information comprises dividing the modified numbers of the pixels by the initial numbers of the pixels.

29. The method of claim 23 wherein the assigning comprises assigning at least substantially all of the pixels of the image into a plurality of different bins.

30. A biological material fouling assessment system comprising:

processing circuitry configured to access image data of an image of a surface of a substrate which has been fouled with biological material;

wherein the image data comprises intensity information regarding a plurality of pixels of the image; and wherein the processing circuitry is further configured to process the intensity information regarding the pixels of the image to generate information which is indicative of an amount of the fouling of the biological material upon the surface of the substrate by using a biofouling growth intensity analysis method that separates a high-contrast signal from the surface of the substrate.

31. A biological material fouling assessment method comprising:

applying a stain to a surface of a substrate which has been fouled with biological material;

after the applying the stain, generating image data of the surface of the substrate including intensity information of a plurality of pixels;

processing the intensity information of the pixels to generate information which is indicative of an amount of the fouling of the biological material upon the surface of the substrate; and wherein the processing comprises comparing the intensity information of the pixels before and after an application of a filter to generate the information which is indicative of the amount of the fouling of the biological material upon the surface of the substrate.

* * * * *

UNITED STATES PATENT AND TRADEMARK OFFICE
CERTIFICATE OF CORRECTION

PATENT NO. : 10,360,667 B2
APPLICATION NO. : 15/240761
DATED : July 23, 2019
INVENTOR(S) : George T. Bonheyo et al.

It is certified that error appears in the above-identified patent and that said Letters Patent is hereby corrected as shown below:

On the Title Page

Page 2, item [56], 1st column, 35th line:
Replace "PCT/US2018/047629" with --PCT/US2016/047629 IPRP--

Page 2, item [56], 1st column, 42nd line:
Replace "Amaral et al., "Stalked Priotozoa Identification by Image Analysis" with --Amaral et al., "Stalked Protozoa Identification by Image Analysis--

Page 2, item [56], 1st column, 45th line:
Replace "Arora et al., "Multilevel Thresholding gor Image Segmentation" with --Arora et al., "Multilevel Thresholding for Image Segmentation--

Page 2, item [56], 2nd column, 37th line:
Replace "Liao et al., "A fast Algorith for Multi-Level Thresholding", Journal" with --Liao et al., "A fast Algorithm for Multi-Level Thresholding", Journal--

Page 2, item [56], 2nd column, 41st line:
Replace "grams", IEEE Transactions on Systems, Man and Cynbernetics vol." with --grams", IEEE Transactions on Systems, Man and Cybernetics vol.--

Page 2, item [56], 2nd column, 43rd line:
Replace "Podlipec et al., "Cell-Scaffold Adhesion Dynamic Measued in First" with --Podlipec et al., "Cell-Scaffold Adhesion Dynamic Measured in First--

Page 2, item [56], 2nd column, 53rd line:
Replace "Sezgin et al., "Survey Over Image Thresholding Techhiques and" with --Sezgin et al., "Survey Over Image Thresholding Techniques and--

Signed and Sealed this
Third Day of March, 2020

Andrei Iancu
*Director of the United States Patent and Trademark Office*

CERTIFICATE OF CORRECTION (continued)
U.S. Pat. No. 10,360,667 B2

Page 2, item [56], 2nd column, 54th line:
Replace "Quantitative Performance Evalution", Journal of Electronic Imaging" with --Quantitative Performance Evaluation", Journal of Electronic Imaging--

Page 2, item [56], 2nd column, 70th line:
Replace "216" with --218--

Page 3, item [56], 1st column, 22nd line:
Replace "Resistance of Marine Coatings Partially Immensed", ASTM Des-" with --Resistance of Marine Coatings Partially Immersed", ASTM Des- --

Page 3, item [56], 2nd column, 19th line:
Replace "Durr et al., "Biofouling and Antifouling in Aquaulture", In Biofoul-" with --Durr et al., "Biofouling and Antifouling in Aquaculture", In Biofoul- --